United States Patent [19]

Moss

[11] Patent Number: 4,601,533
[45] Date of Patent: Jul. 22, 1986

[54] LASER EYE PROTECTION VISOR USING MULTIPLE HOLOGRAMS

[75] Inventor: Gaylord E. Moss, Marina del Rey, Calif.

[73] Assignee: The United States of America as represented by the Secretary of the Navy, Washington, D.C.

[21] Appl. No.: 437,729

[22] Filed: Oct. 29, 1982

[51] Int. Cl.⁴ .............................................. G02B 5/32
[52] U.S. Cl. .................... 350/3.7; 350/3.77
[58] Field of Search ............ 350/3.7, 3.73, 3.77, 350/162.17, 162.21, 162.23

[56] References Cited

U.S. PATENT DOCUMENTS 3,633,988  1/1972  Farrar .................................. 350/3.7
3,930,728  1/1976  Pieuchard et al. ................... 350/3.7

OTHER PUBLICATIONS

Johnson et al., "Laser Eye Protection" Final Tech. Report 8/11/77 to 6/79 on Contract or Grant N62269-77-R-0307, prepared for Naval Air Systems Command, Jul. 1979.

*Primary Examiner*—Bruce Y. Arnold
*Attorney, Agent, or Firm*—Robert F. Beers; Henry Hansen

[57] ABSTRACT

A diffractive radiation shield for protecting eyes and radiation sensitive devices from laser radiation. The shield utilizes one or more holograms disposed on transparent substrates. These holograms consist of spherical holographic fringes recorded in a dischromated gel with which the substrates are coated. The holographic fringes reflect laser radiation which is normal to their respective surfaces. Reflectivity is maximized for a particular wavelength by proper selection of the fringe spacing. The shield may be configured as a visor for an aviator's helmet.

4 Claims, 6 Drawing Figures

LASER EYE PROTECTION VISOR USING MULTIPLE HOLOGRAMS

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

This invention relates to eye protective devices and in particular to a diffractive radiation (laser) shield which utilizes holographic gratings recorded in a gelatin substrate to protect the eye.

As a result of the systems which employ lasers and emit radiation that is damaging to the eyes of personnel utilizing the systems or of personnel in the path of radiation therefrom, eye protective shields that can protect the eyes from incident laser radiation are essential.

Current eye protective devices exclude a wide band of wavelengths and therefore have low transmission and high coloration of a see-through scene. Besides being inherently wideband absorbing, devices which utilize dyes are only applicable to wavelengths for which suitable dyes exist. Reflecting devices which utilize multilayered coatings have optical functions dependent on the device surface shape and are difficult to make protective of both eyes when such coatings are placed on a single shaped substrate.

SUMMARY OF THE INVENTION

Accordingly, it is an object of this invention to provide an improved eye protection device for adequately protecting the eyes from the hazards of incident laser radiation without interfering with normal vision. It is another object of the invention to provide a reflective device that can be positioned adjacent to a wearer's eyes and which maximizes the reflectivity of laser radiation incident to the eyes without distorting and reducing the normal vision. It is yet a further object of the invention to provide a reflector which enables both eyes to be protected from an undesired wavelength of laser radiation over their range of movement even though the region of high diffraction efficiency for each encompasses a limited angular range. It is still a further object of the invention to provide maximum reflection of laser radiation with holograms which have limited angular efficiency range so that other wavelengths are not reflected and therefore the see-through transmission of the device is very good. These and other objects of the invention are achieved as follows. The eye protection device according to the present invention provides for a holographic reflector which reflects laser radiation coincident with the line of sight at a given wavelength. Two dichromate gelatin substrates have recorded thereon holographic volume gratings or fringes and are bonded together at their gelatin surfaces. The device may be configured as a visor for an aviation helmet. The peak diffraction efficiency of one of the holograms always coincides with the line of sight to the eye in question. The recorded holographic fringes create effective holographic mirrors normal to the incident radiation to the eye and maximum reflectivity of the desired wavelength is achieved. Each of the holograms have spherical holographic fringes of increasing radii centered from an average position of each of a wearer's eyes on the attenuated side of the reflector such that separate effective mirrors in each hologram are created normal to paths of incident radiation on lines of sight from a radiation source to that average eye location, within a field of view through the reflector. Each of the holograms has predetermined fringe spacing designed to reflect a given wavelength. The angle of peak diffraction efficiency of one of the holograms always coincides with the line of sight to the eye in question. This utilization of two holograms to reflect radiation of a given wavelength produces a system which provides sufficient angular bandwidth and is therefore suitable for wide angular coverage. The present invention is suitable for wide angular coverage and in addition provides minimum attentuation of the other wavelengths but maximum reflectivity of the given wavelength of laser radiation. Each hologram operates by adding the in-phase reflections from a number of recorded layers of varying index of refraction in the hologram material. Only at particular wavelengths and angles does the radiation add in-phase to reflect from the hologram. Other wavelengths and angles pass through the holographic reflector unattenuated, providing clear see-through except at the reflection wavelength desired.

Other objects, advantages and novel features of the invention will become apparent from the following detailed description of the invention when considered in conjunction with the accompanying drawing.

DESCRIPTION OF THE PREFERRED EMBODIMENT

Figure 1:
FIG. 1 shows a holographic reflector according to the invention shaped as a visor for use on an aviator's helmet.
Figure 2:
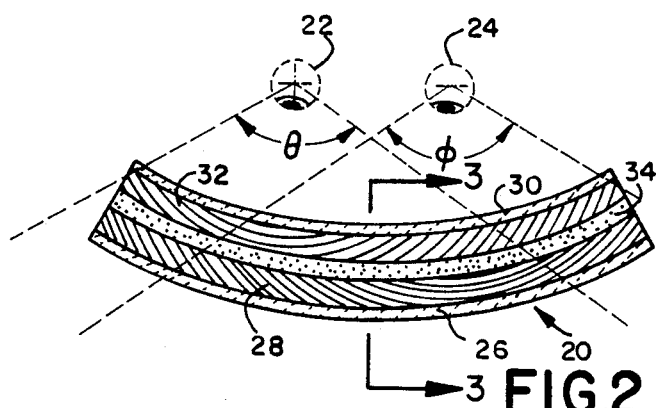
FIG. 2 is a cross-sectional view of the holographic reflector along the line 2—2 shown in FIG. 1.

Referring now to the drawings, wherein like reference characters designate like or corresponding parts throughout the several views, there is shown in FIGS. 1 and 2 a reflector comprised of a first or front substrate 26, which may be comprised of glass or plastic or the like. A first hologram 28 is disposed on the back surface of the first substrate 26. The first hologram may be comprised of a material such as dichromated gelatin or the like. A second or back substrate 30 has a second hologram 32 disposed on the front surface thereof. Holograms 28, 32 are disposed on the respective substrates 26, 30 placed adjacent to each other and are bonded together by means of an adhesive 34 such as transparent epoxy or the like. Holograms 28, 32 and the respective substrate 26, 30 are formed in the same shape so that when bonded together they will result in reflector 20 having a predetermined contour formed in the shape of a visor for attachment to an aviator's helmet.

Figure 4:
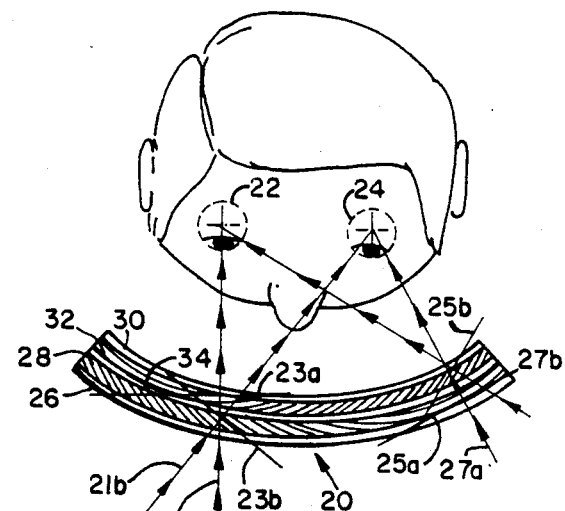
FIG. 4 is a plan view illustrative of the effective mirrors of the holograms of the invention as they reflect incident radiation from the eyes of a wearer.
Figure 3:
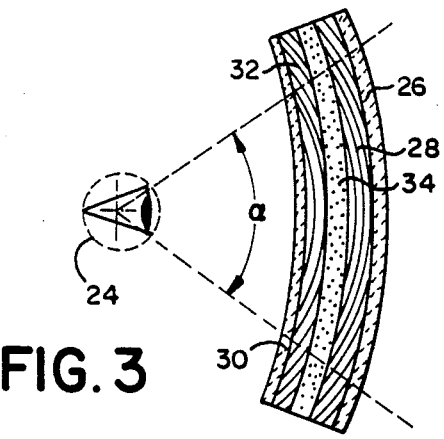
FIG. 3 is a cross-sectional view taken along the lines 3—3 of the holographic reflector shown in FIG. 2.

FIG. 3 shows an expanded cross-sectional view of the holographic reflector 20 along the lines 3—3 as shown in FIG. 2. Referring to FIGS. 2 and 3, holograms 28, 32 contain holographic fringes positioned normal to the average paths of incident radiation from an external laser to average locations to left eye 22 and right eye 24 on the back side of substrate 30. Eye 22 utilizes hologram 32 within the angle $\theta$ to reflect incident radiation since the fringes therein are recorded so that effective mirrors are formed perpendicular to all incident light received by eye 22. Hologram 28 has fringes recorded so that incident laser radiation received within the angle $\phi$ is reflected by effective mirrors created by the fringes normal to the radiation providing maximum reflectivity. The fringe spacing of each hologram 28 and 32 are equal and are determined by the frequency of the laser radiation which is required to be reflected. As shown in FIG. 3, incident radiation from other than horizontal planes are also reflected by virtue of the fringes forming effective holographic reflective mirrors which are normal to incident laser radiation received within the angle $\alpha$. FIG. 4 shows a plan view of the cross section of reflector 20 illustrating effective mirrors 23a, 23b and 25a, 25b in representative positioning of said mirrors with respect to the incident radiation to eyes 22 and 24 respectively. Radiation 21a is reflected by effective holographic mirror 23a formed in hologram 32 by the holographic fringes therein. Eye 24 is protected from incident radiation 27a by effective holographic mirror 25a formed in hologram 28 by the fringes therein. Mirror 23b formed by the fringes of hologram 28 reflects radiation 21b protecting eye 24; likewise incident radiation 27b will be reflected from effective holographic mirror 25b formed by the holographic fringes of hologram 32. A reflection efficiency of 99.9% is provided by the effective holographic mirrors being positioned normal to incident radiation as illustrated in FIG. 4. Holograms 28, 30 reflect laser radiation within predetermined angular ranges $\theta$ and $\alpha$, and $\theta$ and $\alpha$ respectively. As shown in FIGS. 2 and 4, fringes recorded in hologram 28, 32 form concentric arcs with radii centered about eye 24, 22 respectively. As shown in FIG. 3, holograms 28, 32 provide an angular protection range of $\alpha$ therefore making reflector 20 effective over other than one horizontal plane. The recorded fringes form concentric arcs having radii centered at eye 24.

Figure 5:
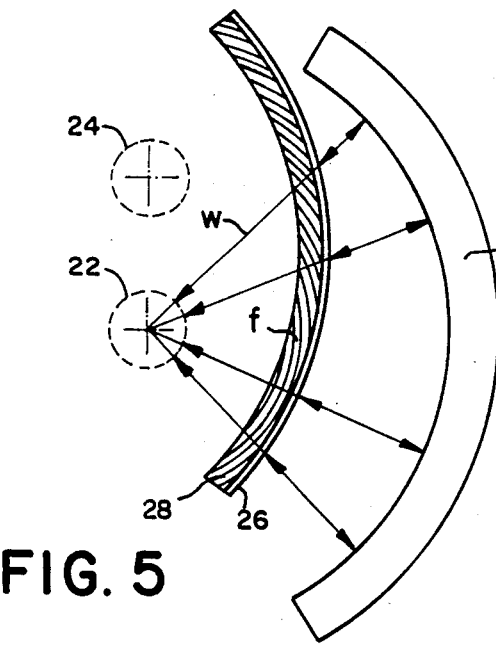
FIG. 5 illustrates an arrangement for recording holographic fringes on a substrate from a point source of radiation from a position at the average location of a wearer's right eye according to the invention.
Figure 6:
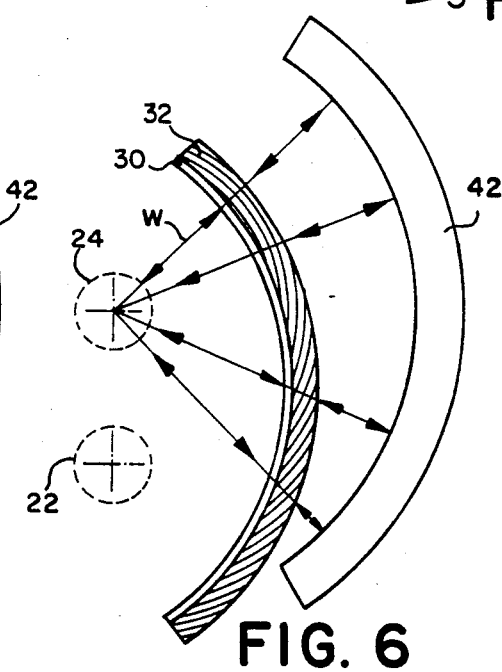
FIG. 6 illustrates an arrangement for recording holographic fringes on a substrate from a point source of radiation from a position at the average location of a wearer's left eye according to the invention.

Hologram construction for achieving a given peak reflection wavelength is generally known in the art. See, for example, Collier et al., *Optical Holography*, Academic Press, 1971, which shows the mechanics of building a hologram to achieve a given peak reflection wavelength. FIGS. 5 and 6 illustrate the method which may be employed to manufacture the holograms utilized in the holographic reflector 20 of the present invention. FIG. 5 shows the construction laser wavefront w emanating from a point at the location of right eye 22. Wavefront w passes through the recording film 28 and through the transparent substrate 26. Wavefront w is then reflected from a mirror 42 which is concentric around eye position 22 so that it is reflected back on itself passing through the substrate 26 in the opposite direction. The interference pattern between the outgoing and reflected waves make an interference pattern in space that is normal to the ray directions or lines of sight from the eye position at 22. These interference patterns or fringes f are recorded on holographic film 28 and form the effective reflective mirrors therein to protect eye 22. In a similar manner the exposure apparatus shown in FIG. 6 in which a wavefront w emanates from the center of the left eye 24 is reflected and forms fringes f in recording film 32 to shield the left eye 24. It can further be seen that only one exposure apparatus need be constructed because by rotating the apparatus of FIG. 5 180° we can form the apparatus of FIG. 6. Additionally instead of rotating the apparatus it is only necessary to rotate the finished holographic element. Note that it is necessary only to construct two holograms in the same apparatus as shown in FIG. 6. One hologram should have the recording gelatin on the convex side of the substrate as shown in FIG. 5, gelatin surface 28. Both recorded holograms can then be cemented together to form the two eye protective device shown in FIG. 2.

For the purpose of completeness, and as an example of a specific design, a holographic reflector constructed according to the invention utilized holographic fringes recorded normal to incident radiation 5 and provided a 99.9% rejection efficiency of laser radiation at 0.5041 microns over a 24.5° angular range but yet allowed 90 percent photopic see-through transmission of desirable wavelengths. The protective visor shilded the eye over a 4 centimeter diameter region centered 3 centimeters from the midpoint between the eye. The 4 centimeters included a two centimeter width of the exposed eye region, about one centimeter to accommodate individual eye position variation and one centimeter horizontal visor position tolerance. The visor provided an angular shielding range of approximately 30° requiring it to be placed about 80 centimeters from the eye in order to shield the four centimeter region of the eye.

Some of the many advantages of the present invention should now be readily apparent. The invention allows for a holographic reflection diffraction grating that can be put on a pilot's visor and that would reject 99.9% of a specific visible laser wavelength and still have 90% photopic see-through transmission. The invention will provide maximum reflection of laser radiation with holograms which have limited angular efficiency range. A further advantage of the invention is that holographic gratings can be fabricated on a visor of arbitrary shape since fringe surfaces are normal to the incident radiation.

Obviously, many modifications and variations of the present invention are possible in view of the above teachings. It is therefore to be understood that within the scope of the appended claims, the invention may be practiced than otherwise as specifically described.

What is claimed is:

1. A diffractive radiation shield for protecting a plurality of separated points displaced from one side of the shield from laser radiation of a desired wavelength incident on the other side of the shield on lines from the radiation source through said points comprising:
    a like plurality of coextensive transparent substrates to cover all of the points;
    recording mediums respectively disposed on one side of said substrates, each of said mediums having spherical holographic fringes of increasing radii which are centered about respective ones of the points and spaced according to the desired wavelength; and
    optically transparent adhesive between said mediums forming a contiguous lamination thereof.

2. The shield according to claim 1 wherein said recording medium comprises:
a dichromated gelatin.

3. A visor for protecting the eyes of a wearer displaced behind the visor from laser radiation of a desired wavelength incident on the front of the visor on lines of sight from the radiation source through the eyes comprising:

two coextensive transparent substrates, each arcuately shaped to cover both eyes;

two recording mediums respectively disposed on each of the facing surfaces of said substrates, each of said mediums having spherical holographic fringes of increasing radii which are centered about respective ones of the eyes and spaced according to the desired wavelength; and optically transparent adhesives between said mediums forming a contiguous lamination thereof.

4. The visor according to claim 3 wherein said recording medium comprises:
a dichromated gelatin.

* * * * *